(12) United States Patent
Merkin

(10) Patent No.: US 7,657,442 B2
(45) Date of Patent: *Feb. 2, 2010

(54) HEALTH CARE ADMINISTRATION METHOD

(76) Inventor: Richard Merkin, 18107 Sherman Way, Reseda, CA (US) 91335-4564

( * ) Notice: Subject to any disclaimer, the term of this patent is extended or adjusted under 35 U.S.C. 154(b) by 876 days.

This patent is subject to a terminal disclaimer.

(21) Appl. No.: 10/615,640

(22) Filed: Jul. 8, 2003

(65) Prior Publication Data

US 2005/0010436 A1 Jan. 13, 2005

(51) Int. Cl.
*G06Q 10/00* (2006.01)
*G06Q 50/00* (2006.01)

(52) U.S. Cl. ........................................................ 705/2
(58) Field of Classification Search .................. 705/2–4
See application file for complete search history.

(56) References Cited

U.S. PATENT DOCUMENTS

| | | | | | |
|---|---|---|---|---|---|
| 5,890,129 | A | * | 3/1999 | Spurgeon | 705/4 |
| 5,937,387 | A | * | 8/1999 | Summerell et al. | 705/2 |
| 6,067,524 | A | | 5/2000 | Byerly | |
| 6,177,940 | B1 | * | 1/2001 | Bond et al. | 434/262 |
| 6,240,394 | B1 | | 5/2001 | Uecker | |
| 6,341,265 | B1 | * | 1/2002 | Provost et al. | 705/4 |
| 6,343,271 | B1 | | 1/2002 | Peterson et al. | |
| 6,735,569 | B1 | | 5/2004 | Wizig | |
| 6,820,058 | B2 | | 11/2004 | Wood et al. | |
| 6,824,052 | B2 | | 11/2004 | Walsh | |
| 7,016,856 | B1 | * | 3/2006 | Wiggins | 705/2 |
| 7,039,458 | B2 | | 5/2006 | Ueda et al. | |
| 2001/0037214 | A1 | | 11/2001 | Raskin et al. | |
| 2002/0007290 | A1 | | 1/2002 | Gottlieb | |
| 2002/0019754 | A1 | | 2/2002 | Peterson et al. | |
| 2002/0026105 | A1 | | 2/2002 | Drazen | |
| 2002/0035316 | A1 | | 3/2002 | Drazen | |
| 2002/0062226 | A1 | | 5/2002 | Ito | |
| 2002/0120466 | A1 | * | 8/2002 | Finn | 705/2 |
| 2002/0120471 | A1 | | 8/2002 | Drazen | |
| 2002/0149616 | A1 | | 10/2002 | Gross et al. | |
| 2003/0074228 | A1 | | 4/2003 | Walsh | |
| 2003/0078811 | A1 | | 4/2003 | Cole et al. | |
| 2003/0078813 | A1 | | 4/2003 | Haskell et al. | |
| 2003/0078911 | A1 | | 4/2003 | Haskell et al. | |
| 2004/0186744 | A1 | | 9/2004 | Lux | |
| 2006/0080146 | A1 | | 4/2006 | Cook et al. | |
| 2006/0085222 | A1 | | 4/2006 | Huang et al. | |

* cited by examiner

*Primary Examiner*—Gerald J. O'Connor
*Assistant Examiner*—Sheetal R Rangrej
(74) *Attorney, Agent, or Firm*—Stetina Brunda Garred & Brucker

(57) ABSTRACT

Health care administration methods are disclosed that substantially conserve the utilization of health care resources available to care for a specified patient population. Initially, a patient population is generated whereby each patient therein is assigned a risk based upon a retrospective and postspective assessment of the patient. Once the patient population is generated, utilization management practices are implemented that restrict utilization of health care resources without adversely impacting clinical outcome or quality of care until such utilization of resources is deemed medically warranted. A network of health care providers and health care providing institutions administers health care to the population according to methods of the present invention based upon primary care decision making practices utilizing the most cost-effective management practices and minimizing the use of specialists and in-patient/out-patient services whenever applicable.

23 Claims, 3 Drawing Sheets

HEALTH CARE ADMINISTRATION METHOD

CROSS-REFERENCE TO RELATED APPLICATIONS

Not applicable

STATEMENT RE: FEDERALLY SPONSORED RESEARCH/DEVELOPMENT

Not applicable

BACKGROUND OF THE INVENTION

The present invention is directed to methods for administering health care resources amongst patients within a patient population and, more particularly, to generate a patient population and conserve the medical resources utilized to care for such population by utilizing methods that continuously monitor and evaluate health care delivery.

As is well known, the utilization of health care resources has and continues to be grossly inefficient. Generally, the current administration of health care in the United States is subject to tremendous abuse, both by patients, on one hand, and health care providers and health care providing institutions, on the other. With respect to the latter, it is well-known that health care providers and health care providing institutions, such as hospitals, clinical laboratories, outpatient and rehabilitation facilities, engage in capricious billing practices that enable such providers and institutions to charge for a multiplicity of services that may be available under a single clinical event. In this regard, to the extent a particular type of medical service is rendered by a professional provider, the same is typically identified by a CPT (Current Procedural Terminology) code, which describes the medical service by use of a numeric code utilizing an accepted method developed by the American Medical Association Problematic with such practice, however, is that often times health care providers and health care providing institutions attempt to seek reimbursement, whether it be from an insurance company, health maintenance organization or government sponsored health care program, such as MediCare, for two or more separate services that are actually integrated into one clinical event. For example, the physician drawing blood for purposes of conducting lab work may attempt to have the procedure to draw blood charged separately and in addition to the services associated with the laboratory blood testing. Other well-known abuses occur when health care providers and institutions attempt to seek reimbursement for procedures and tests that are performed by non-physicians, such as nurses or technicians performing such procedures but seek reimbursement for the services of a physician.

Additionally wasteful practices include duplicative and unnecessary tests and procedures. Along these lines, many medical procedures are performed by specialists (who command higher rates of reimbursement) that oftentimes can be performed by a non-specialist, and in particular a patient's primary care physician. Likewise, many such procedures and tests are performed in an in-patient facility, as opposed to an out-patient facility, which thus substantially increases the costs associated with the applicable service. Furthermore, there is a tendency among health care providers and institutions to render care that fails to take into account lower cost alternatives that utilize cost-effective out-patient facilities, and/or competitive pricing practices that eliminate or substantially limit the utilization of specialists, the performance of unnecessary tests, excessive office visits, and the like.

In addition to health care providers and institutions, patients themselves contribute substantially to the cost and ineffective utilization of health care resources. As is well-known, patients can and frequently do seek unnecessary medical treatment or otherwise attempt to influence the judgment of the health care provider by demanding that unnecessary tests or procedures be performed, that the patients have access to specialists or particular medications, and/or seek in-patient services in situations where the patient's clinical condition clearly does not justify such level of care. Such potential abuses are particularly likely where patients are allowed the discretion to directly access specialists, as is typical in several well-known health care insurance plans, such as Blue Cross and Blue Shield, which thus bypasses the critical role played by the primary care physician in making an initial assessment of a patient's condition and whether the same truly warrants the attention of a particular specialist, and not to mention the specialist best suited to handle a particular condition.

In order to counter such wasteful and abusive practices by both health care providers, health care providing institutions, and patients, attempts have been made to implement certain practices and procedures to contain health care costs and conserve the utilization of health care resources. Exemplary of such attempts include requiring prior authorization and approval by an intermediate entity, such as a health maintenance organization or health insurance plan, to the extent a physician seeks to take a specified action, such as perform surgery, order a medical supply or refer the patient to a specialist. Also utilized are the practices of bundling, whereby a physician is paid a single payment for two or more medical services, and capitation whereby a health care provider is paid a set dollar amount as determined by a per member, per month calculation to deliver medical services to a specific patient population (i.e., members of a health maintenance organization). Still further examples include the use of preferred provider discounts, which encourage the use by patients of specific health care providers, and usual and customary reductions, which impose a reduction in the payment of medical services rendered as deemed justified by a health plan or insurance company based upon what is considered to be the justified value of such services as rendered in a particular geographical area.

Despite such attempts, however, there has yet to be devised any type of health care administration system or method that substantially conserves utilization of health care resources that as a consequence can dramatically lower the costs associated in providing care to a specific patient population. Such attempts have likewise failed to maintain any degree of consistent quality of health care insofar as prior art cost containment practices have been and continue to be riddled with "loopholes" and insufficient cost-deterrent mechanisms necessary to conserve and optimally utilize a finite amount of health care resources.

As a result of the aforementioned abuses and inefficiencies associated with the utilization of health care resources, the cost of health care has and continues to increase substantially while the quality of the health care provided has not necessarily improved. As such, there is a substantial need in the art for a health care administration method that is operative to effectively and efficiently utilize health care resources to administer care to a patient population as compared to conventional practices. There is additionally a need in the art to generate a patient population that takes into account a multiplicity of factors that facilitate the optimal utilization of health care resources utilized to care for a given patient population that is also continuously evaluated to maximize the efficient use of resources. There is still further a need in the art for such a method that substantially eliminates abusive billing practices, the performance of unnecessary procedures, the unnecessary use of specialists, minimizes utilization of out-patient and in-patient services, and is generally effective in eliminating the wasteful practices associated with the allocation and utilization of health care resources without adversely compromising clinical outcomes or quality of care.

BRIEF SUMMARY OF THE INVENTION

The present invention specifically addresses and alleviates the above-identified deficiencies in the art. In this regard, the present invention is directed to health care administration methods that are exceptionally effective in conserving the utilization of health care resources to administer health care to a specified patient population. The methods of the present invention are further operative to provide substantially more cost-effective health care than prior art systems but further does not sacrifice the quality of health care or clinical outcomes within the patient population.

According to the preferred methodology, the process comprises the initial step of patient enrollment within the patient population. According to such initial step, an individual seeking enrollment submits data indicative of the individual's demographics, as per conventional health insurance application procedures. Such data is carefully evaluated, and may involve an interview with the individual to determine whether or not such individual meets any applicable eligibility criteria necessary to become a member of the patient population. To the extent patient is allowed to enroll, the patient is assigned a risk based upon a prospective and retrospective assessment of the patient's health. Such assessment is ongoing for the duration the patient remains within the patient population. Based upon such assessment, an estimated cost is determined that is indicative of the cost necessary to provide health care for that particular individual according to the implementation of the health care delivery methods of the present invention. As per conventional practice, such estimated costs may be utilized to derive a premium to be paid by the individual for care to be provided.

With respect to the health care delivery practices of the present invention, it is contemplated that a network of health care providers and health care providing institutions, including in-patient and out-patient care facilities, will be utilized that are operative to provide an integrated health care delivery system. With respect to the health care providers, the same will comprise primary care physicians and specialists, the latter of which are selectively made available to patients within the patient population. Other than patients having medical necessities that require immediate access to medical services, all patients within the patient population seeking health care treatment must first be assessed by a primary care physician. To the extent the primary care physician requests additional services (i.e., beyond the initial assessment), such request is submitted in the form of a single code, which preferably takes the form of a conventional CPT code, which is then evaluated for appropriateness (typically by a hospitalist, physician or a designated case manager trained in such execution processes) as determined by a variety of factors including the amount sought by the health care provider for rendering such services associated with patient treatment and/or the anticipated cost of the treatment compared to the anticipated patient outcome, the likelihood that such requested services will effectively change the clinical management of the patient, and whether such requested services may be rendered through more cost-effective facilities and/or health care providers that are within, or if necessary not within, the network. Importantly, such assessment made by the primary care physician will be screened to determine whether or not the same strictly adheres to the coding practice to thus prohibit duplicative billing and unbundled service. According to a preferred embodiment, such evaluation further takes into consideration whether or not the health care provider stands to gain any future financial benefit in rendering the requested services at some point in time in the future.

To the extent further care must necessarily be rendered, a clinical management plan is implemented that is closely scrutinized and continuously evaluated such that only essential and the most cost-effective health care practices available within the network are implemented. To that end, all services rendered are subject to authorization and must strictly adhere to a coding practice that is continuously assessed for appropriateness in terms of efficacy and cost-effectiveness. Importantly, the coding practice implemented as part of the practice of the present invention relies predominantly upon the use of single CPT codes for use determining authorization of medical services to be rendered, as well as the fees at which such services are to be rendered. Stringent measures are implemented to insure abusive billing practices are avoided.

Such practices are further implemented and for every aspect of health care services rendered amongst patients within the patient population. In this regard, such utilization management practices, and in particular the coding practices of the present invention are applied in relation to both in-patient and out-patient services, whether it be home based care, emergency/urgent care or skilled nursing care. To that end, it is expressly contemplated that the methods of the present invention can be implemented as part of a fully integrated health care delivery system.

The methods of the present invention are further operative to assess the efficacy of utilization management by providing means to continually evaluate the performance of the health care providers participating in the network based upon their adherence to the coding practices, as continuously evaluated, as well as how cost-effectively those patients have been treated by a particular health care provider. For example, a participating network primary care physician can be evaluated based upon the number of patients he or she is seeing relative the degree of health care resources utilized, whether it be referrals to specialists, requests for additional tests, or authorization to render additional services or procedures. Such data generated from health care providers participating within the network can further be utilized to identify further cost-saving measures, such as the cost-effectiveness of in-patient and out-patient services offered within the network, as well as the total cost of services rendered per patient within the patient population.

Advantageously, the methods of the present invention can be implemented in an extremely cost-effect manner, whether it be over a small or large patient population. The methods of the present invention can further advantageously be deployed irrespective of any demographics associated with a given health care system due to the precise standardization of those services that are ultimately rendered to the patients within the patient population, as well as the continual evaluation as to whether such medical services are, in fact, truly necessary and cost-effective. Still further, given the precise nature by which medical services are rendered, not to mention the scrutiny applied in determining the appropriateness of those services, the methods of the present invention are particularly well suited to substantially eliminate fraud and abusive practices typically associated with conventional health care delivery systems and further minimize the ability of the patients participating within such framework to authorize or otherwise influence excessive or unnecessary utilization of medical resources.

BRIEF DESCRIPTION OF THE DRAWINGS

These as well as other features of the present invention will become more apparent upon reference to the drawings.

DETAILED DESCRIPTION OF THE INVENTION

Figure 1:
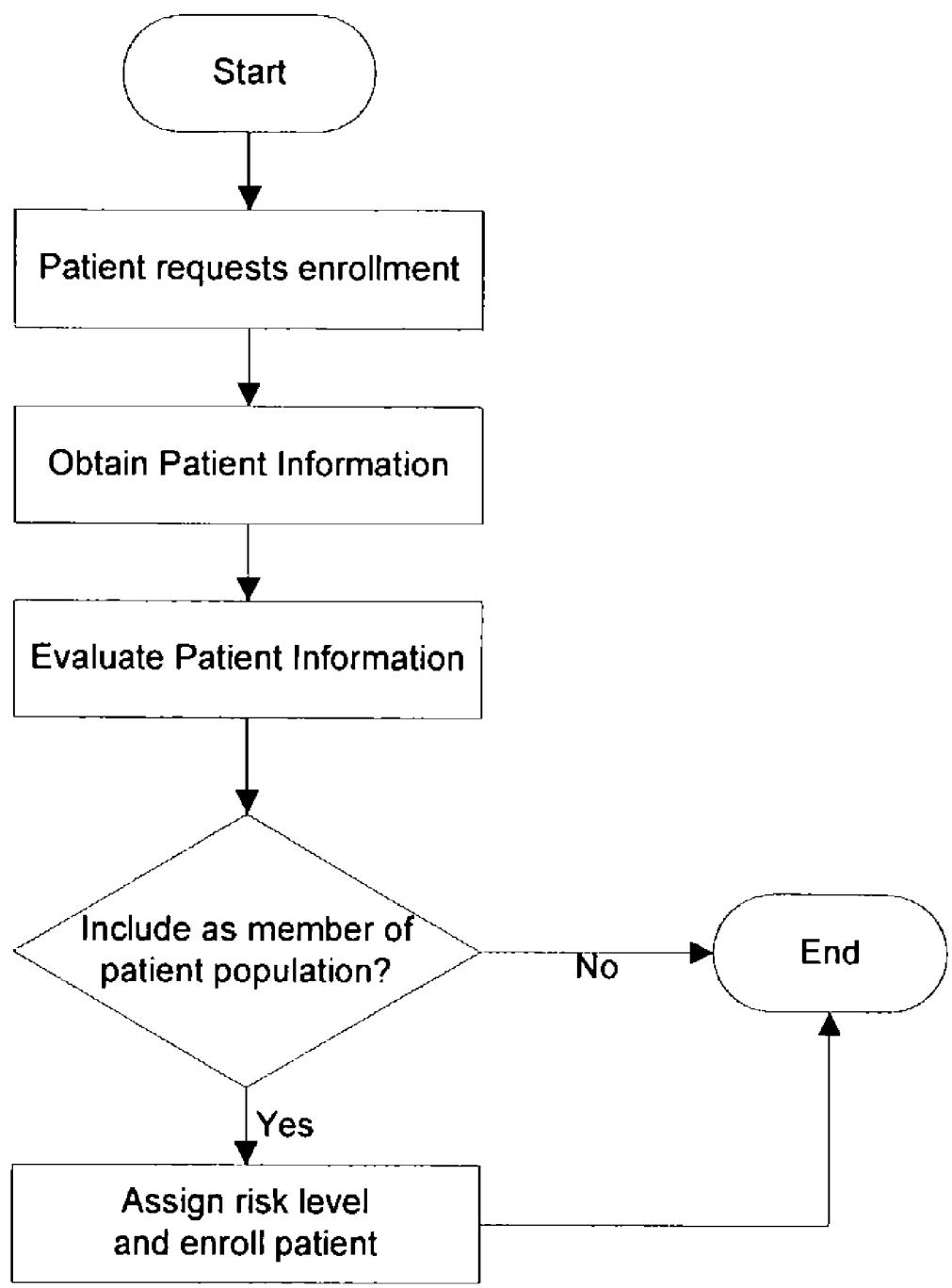
FIG. 1 is a flow chart depicting the steps for enrolling a patient as a member within a patient population.

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

The present invention is directed to methods for conserving the utilization of health care resources to thus enable a population of patients to be cared for in a manner that is substantially more efficient and effective than prior art methods, particularly with respect to those utilization practices of most health insurance plans, health maintenance organizations, and government sponsored health care programs, such as MediCare, as practiced in the United States while at the same time optimizing the quality of the care provided to those patients within the patient population. To achieve that end, the present invention comprises methods that are operative to generate a patient population whereby each patient within the patient population, after careful evaluation, is assigned a risk, which is thereafter continuously assessed based upon that particular patient's health care needs.

A network or infrastructure of health care providers and health care providing institutions is utilized in the practice of the present invention to administer health care to those patients within the patient population. Such health care providers and institutions, as will be appreciated by those skilled in the art, will comprise an integrated medical delivery system consisting of physicians and in-patient and out-patient facilities capable of comprehensively delivering medical treatment to those patients within the patient population according to a strict protocol discussed more fully below. In this regard, the present invention relies upon a procedural framework whereby primary care physicians are responsible for the initial assessment of those patients within the patient population seeking treatment that must closely adhere to a strict coding procedure that dictates what particular type of medical services are to be rendered in relation to a specific patient's condition, as well as the amount the primary care physician is to be reimbursed due to the services rendered in assessing and/or treating such patient for such condition.

To the extent additional care must necessarily be rendered beyond the capability of the primary care physician, careful assessment is made to those additional services necessary to treat the condition of the patient. In this regard, and as discussed more fully below, strict coding practices are implemented that regulate what treatment is to be provided to a particular patient as the patient continuously undergoes evaluation from both the standpoint of the effectiveness of the treatment sought to be implemented and the cost-effectiveness of such treatment.

The methods of the present invention can be implemented as part of any health care delivery system, including any conventional public or private system, such as a health maintenance organization, health plan or government sponsored program, that is responsible for overseeing the utilization of health care resources of an integrated delivery system to administer health care to a patient population. If implemented correctly, the methods of the present invention can optimally administer and substantially conserve the utilization of health care resources to thus enable cost-effective services to be rendered. Indeed, it is contemplated that the health care administration methods of the present invention can and will serve as a model from which existing health care administration systems can emulate to not only conserve resources, but where applicable, substantially increase profitability.

Bearing the foregoing principals in mind, there is schematically depicted in FIG. 1 a flow chart of the steps utilized to generate a patient population 10, the latter defining a group to which the health care administration methods of the present invention are applied. In this regard, key to the practice of the present invention is the existence of a known population of patients to which a finite amount of health care resources are to be made available. As is well-known in the art, the attainment of more efficient and cost-effective health care delivery is dependent upon the degree of utilization of such health care resources amongst a given patient population, as well as the cost per patient necessary to support the health care delivery infrastructure necessary to provide such care.

As illustrated, the process by which the patient population is generated is initiated by the enrollment of a potential patient 12. As per conventional practices, such as those utilized by health maintenance organizations and well-known health plans such as Blue Shield and Blue Cross, information is obtained from the potential candidate via step 14 that pertains to the potential patient's age, sex, ethnicity, medical history, occupation and other demographics. Importantly, the information obtained and evaluated in step 16 will include information related to the number of emergency room visits and number of hospitalizations and readmissions, particularly with respect to the twelve month period preceding enrollment. Further specified information will include patient pharmacy records, medication compliance and, where applicable, the current condition of any disease that the potentially enrolled patient may have, such as hypertension or diabetes. It is further contemplated that such potential patient will be interviewed to thus enable information to be gleaned first hand and assure accuracy of the information provided.

Once such information is obtained, the same is evaluated 16 extensively for purposes of estimating future utilization patterns for such patient. In this regard, in addition to a retrospective analysis which assesses the current health of the potentially enrolled patient based upon the patient's history, a prospective assessment is made which anticipates the likely future professional and institutional costs necessary to provide care for such patient, and takes into consideration potential hospital and emergency room visits, potential need for skilled nursing facilities, the use of ambulances, and clinically intensive procedures, such as dialysis.

Based upon the information obtained from the evaluation made with respect thereto, a decision is made at step 18 as to whether or not to include the individual as part of such patient population. To the extent such individual does not meet any applicable eligibility criteria or cannot otherwise become a member of the patient population, such individual is denied enrollment and such process ends 20. In this regard, it is contemplated that eligibility criteria may be established that can limit the number of types of individuals eligible to become part of the patient population. In this regard, to the extent an individual is not eligible, which may be warranted based upon a pre-existing condition or other justifying circumstance, the denial of enrollment may be deemed warranted in certain applications of the present invention.

On the other hand, to the extent the patient seeking enrollment meets all applicable eligibility requirements, the patient is included as part of the patient population. As part of the enrollment process, however, it is presently contemplated that each member being enrolled will be assigned a risk level 22 commensurate with the current state of health of the individual, as well as the anticipated future health of the individual. In order to accurately assess the latter factor, the methods of the present invention expressly contemplate that an ongoing evaluation of each enrolled member within the patient population will be made on a periodic basis, such as six months for example, to monitor trends in utilization and whether or not a patient deviates in terms of anticipated health care needs. Along these lines, it is contemplated that depending on the prospective assessment made for a given enrolled patient, a reassignment of risk may be made so long as the patient is a member of the patient population.

As will be appreciated by those skilled in the art, by assigning a risk to each patient within the patient population, an estimate can be made with respect to the anticipated resources to care for such individual, as well as the anticipated costs associated with the delivery of such care. As such, it is contemplated that the assignment and assessment of risk can be utilized as a basis for determining such matters such as setting premium pricing, enrollment fees, co-payment amounts, deductibles, fee schedules and other cost structures well-known to those skilled in the art and utilized in conventional health care delivery systems with which the methods of the present invention may be utilized.

Figure 2:
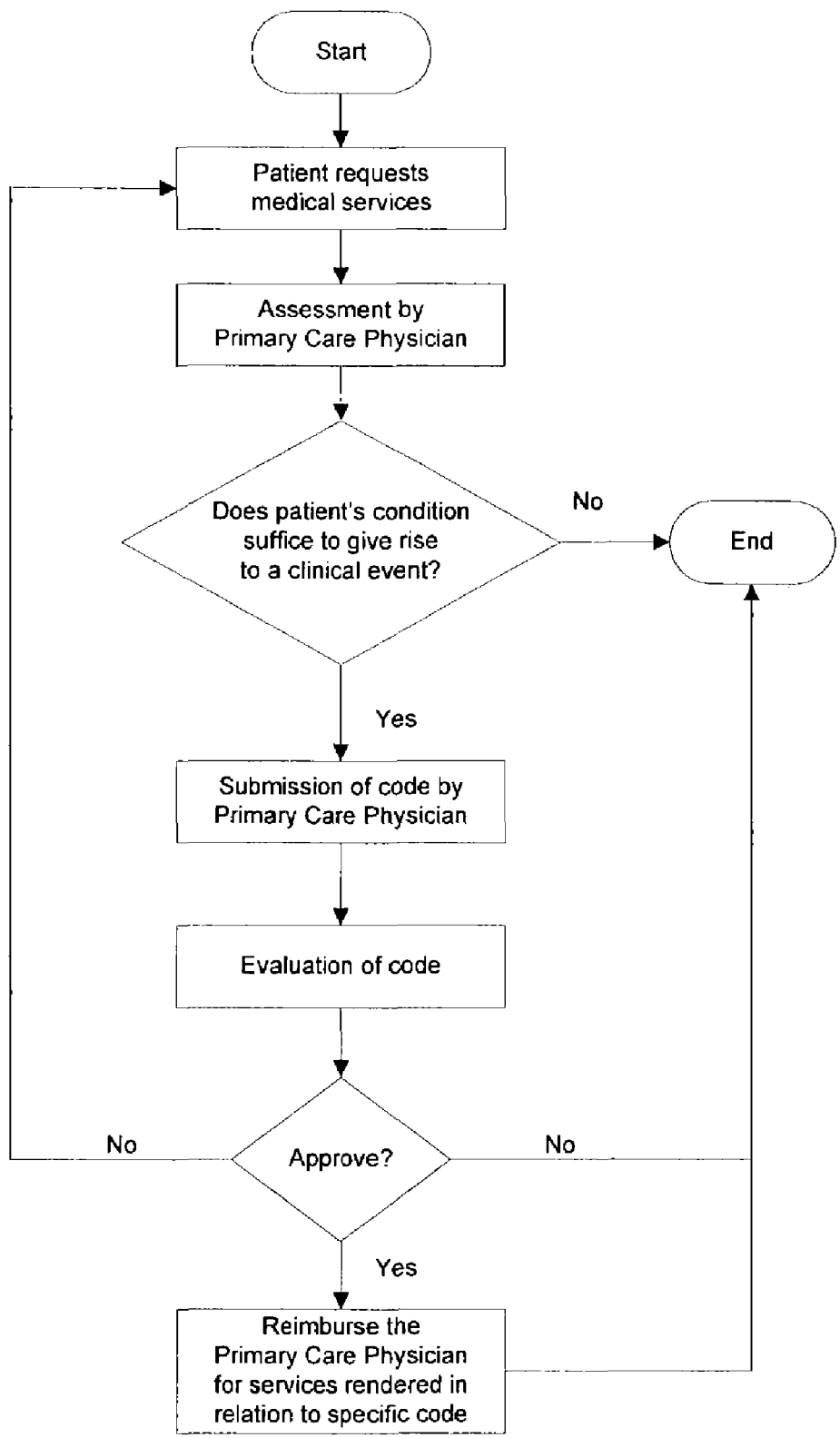
FIG. 2 is a flow chart depicting the steps for providing authorized medical services to a patient within the patient population by a health care provider, namely, a primary care physician.

Referring now to FIG. 2, there is schematically illustrated the steps for generally rendering medical services to patients within the patient population. In this regard, and as discussed above, it is contemplated that the present invention will utilize a network of health care providers and health care providing institutions which are capable of providing comprehensive care to patients within the patient population. Such network will include the infrastructure necessary to provide an integrated delivery of health care to all members within the patient population. In this regard, such infrastructure will include hospitals, skilled nursing facilities, specialized care and treatment centers and a network of health care providers comprised of primary care physicians and specialists having expertise in particular fields of medicine, such as cardiology, urology, dermatology, or any other recognized medical specialty. Along these lines, it is expressly contemplated that such infrastructure can incorporate any of a variety of conventional health care institutions to administer health care to patients within the patient population. For example, it is contemplated methods of the present invention may utilize independent practice associations or exclusive provider organizations that are contractually bound to render medical services pursuant to the methodology of the present invention. Irrespective of the specific framework of health care providers utilized to deliver care to patients within the patient population, however, in all such contemplated arrangements the distinction will be made between primary care physicians and specialists, whereby the latter, along with utilization of additional in-patient and out-patient services, is strictly prohibited unless medically justified, discussed more fully below.

In the initial step in such process, a patient requests medical services 32, typically by making arrangements for an office visit with a primary care provider participating in the health care network. It is important to the practice of the present invention that every attempt be made to insure that patients seeking medical services from within the network be assessed initially by a primary care physician and not otherwise allowed direct access to specialty physicians and/or in-patient and out-patient services and the like until such time there is access to such specialty physicians and/or in-patient or out-patient services are deemed necessary.

The patient is then initially assessed 34 by the primary care physician exercising independent judgment and providing a diagnosis of and/or proposed treatment for the patient's condition. Based upon such assessment, a decision is made as to whether or not the patient's condition actually gives rise to a clinical event 36, which as used herein is meant to broadly encompass any type of test, referral or treatment outside of the initial assessment made by the primary care physician. For purposes of the present invention, each and every clinical event will be specifically categorized according to a unique numeric code, which will preferably comprise the conventional use of CPT (Current Procedural Terminology) codes that are well-known in the art and correspond to those accepted methods developed by the American Medical Association to describe standardized medical services by use of a numeric code.

To the extent the patient's condition does not suffice to give rise to such a clinical event no further action is taken outside of the office visit and no medical services are rendered 38.

On the other hand, to the extent the patient's condition does give rise to a clinical event, the primary care physician will submit the applicable code 40 indicative of the medical services to be rendered in relation to such condition. Importantly, given the comprehensive nature of CPT coding practices, as well as the standardized delivery of specific tests, treatments and other medical services rendered in the art, it is contemplated that one, and only one, specific code will be submitted by the primary care physician as part of such process. In this respect, the submission of multiple codes is expressly sought to be eliminated through the methods of the present invention, which are well-known in the art to promote abusive and duplicative billing practices whereby the services rendered in relation to a single clinical event, as contemplated by the present invention, are segregated into a multiplicity of sub-categories or involve services not rendered by a physician for purposes of increasing the reimbursement to be paid to the health care provider. In this regard, in addition to selectively controlling access to health care resources within the network, the present invention is further operative to contain the costs associated with the delivery of health care by strictly regulating the ability of a health care provider to be reimbursed for services rendered in relation to providing health care.

Following the submission of what is preferably a single code by the primary care physician in relation to the patient's condition and services rendered in relation thereto, an evaluation 42 is made as to the appropriateness of the code submitted. Such evaluation is made by a knowledgeable hospitalist, physician or case manager having a thorough understanding of the administration of health care who decides whether or not a submitted code is appropriate based upon a multiplicity of factors, which include the effectiveness or clinical importance of the services rendered in relation to the clinical event, whether the submitted code for which reimbursement is sought is applicable to those health care services which are covered, (i.e., fall within the scope of) health care to be provided to patients within the patient population, and whether the applicable code is susceptible to duplicative and/or unbundled billing practices or otherwise provide any financial interest to the primary care physician that exceed the scope of care provided.

Based upon the evaluation 42 made, a decision 44 is made as to whether or not to approve the code submitted by the primary care physician and whether or not the primary care physician can be paid or reimbursed for the value commensurate for the medical services corresponding to that of the submitted code. Such approval process has three potential outcomes, namely, a first outcome whereby the code submitted by the primary care physician is deemed completely inappropriate and denied in its entirety. As a consequence, the process ends 38. Alternatively, approval may be denied with the primary care physician being asked to reassess or otherwise restart the assessment procedure 34. Exemplary of such circumstances where reassessment may be necessary involve matters where the code submitted by the primary care physician reflects services that are not supported by third party literature, provide a low probability of favorable outcome, are cost-prohibitive or otherwise unnecessary. In such circumstances, the primary care physician will reassess the patient in light of the grounds for denying approval and afforded the opportunity to submit an alternative code that is commensurate with the appropriate level of services that should have been rendered in order to address the patient's condition.

In the third possible outcome, the submitted code is approved. In such circumstances, the services rendered as reflected by the submitted code will be deemed payable 46 and, pursuant to conventional health plan practices, be considered a covered expense that will be paid by the applicable entity, such as a health maintenance organization or insurance company, at the allowed amount, which may be determined pursuant to conventional medical service pricing practices.

Figure 3:
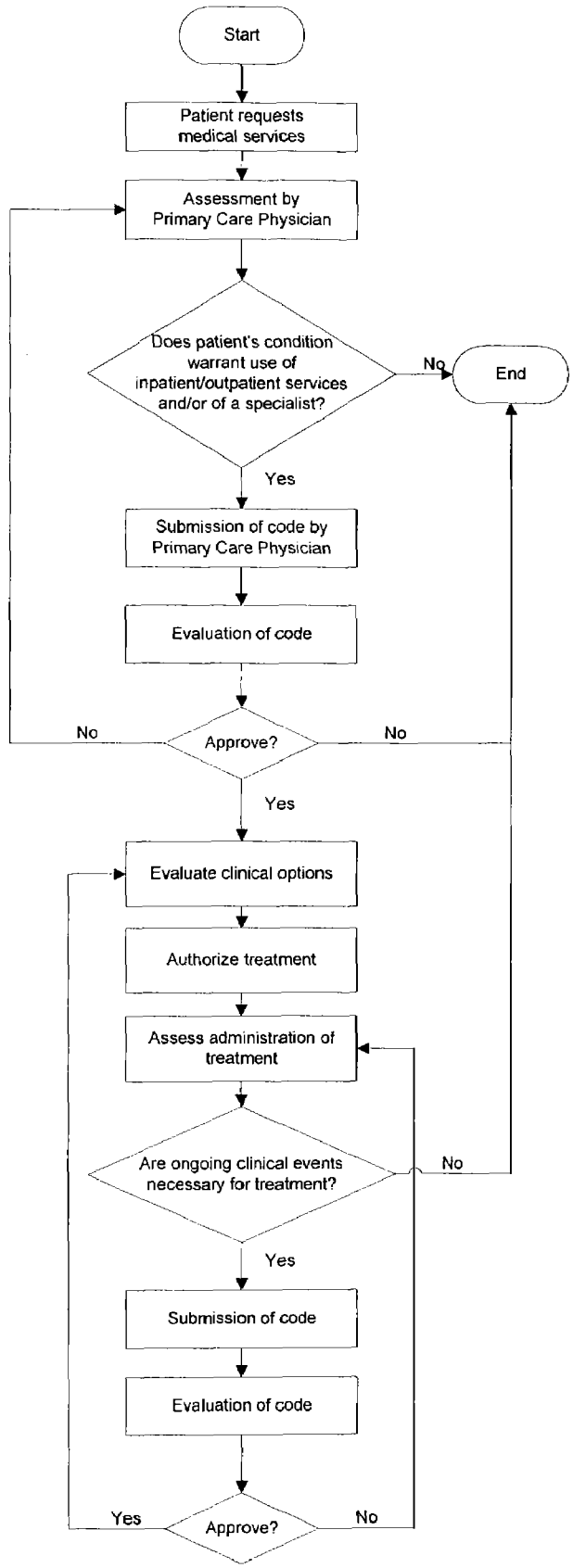
FIG. 3 is a flow chart depicting the steps for providing authorized medical services to a patient within the patient population that contemplates the possible utilization of in-patient or out-patient services, or the use of specialists.

Referring now to FIG. 3, there is shown a comprehensive resource utilization flow chart embodying the principles of the present invention that are applicable to facilitate the conservation of health care resources where there is a potential need to use in-patient or out-patient services in order to treat a particular medical condition of a patient within the patient population, as well as possibly involve the use specialty physicians. As depicted, such procedure 60 initially mimics that discussed above with respect to FIG. 2 in relation to an initial office visit by a patient within the patient population to request service 62 from a primary care physician. As discussed above, it is highly preferred in the practice of the methods of the present invention that all patients within the patient population first be assessed by a primary care physician 64. Based upon such assessment 64, a determination 66 is made as to whether or not the patient's condition warrants the use of in-patient/out-patient services and/or the use of a specialist physician. To the extent the primary care physician deems the utilization of such resources unnecessary, the process ends 68. To the extent the primary care physician feels otherwise, the primary care physician submits a code 70 indicative of the patient's condition, as well as the corresponding clinical event that warrants the use of such additional resources. As per the practices discussed above, it is highly preferred, and may often times be deemed mandatory, that a single code be utilized, which again may take the form of conventional CPT code, that precisely identifies the specific services necessary to address the patient's condition. Any submission of multiple codes, unless thoroughly substantiated, will be highly disfavored, and particularly so to the extent the services requested as part of such submitted codes involve the utilization of excessive and unnecessary tests, medical procedures and the like.

The appropriateness of the code submitted is evaluated 72 based upon the multiplicity of factors, as discussed above. In this regard, the submitted code is evaluated to determine whether or not the requested services are appropriate for the clinical condition being treated, whether the requested services are cost-effective, essential and likely to produce a favorable outcome, as well as whether or not the coding is susceptible to any type of abusive billing practices, either by the primary care physician submitting such code or by the specialists or other entities that may possibly render additional services to treat the condition at issue. Along these lines, and as discussed above, it is contemplated that the entity responsible for making such evaluation will be thoroughly skilled in the evaluation of medical conditions and the treatment options available within the network to treat the same. In this regard, it is contemplated that in order to effectively practice the methods of the present invention will require a sufficient staff of hospitalists and case managers operative to provide appropriate evaluation of any and all codes submitted seeking reimbursement and/or authorization to utilize resources beyond those provided by the primary care physician.

Based upon the evaluation 72, a decision 74 to approve the use of in-patient/out-patient services and/or specialists (or any other service that must necessarily be rendered beyond that capable of the primary care physician) involves the same three potential outcomes. First, the submitted code requesting additional services or referral to a specialist is not approved to the extent the service referral sought to be authorized is completely inapplicable, excessive, unlikely to produce a favorable outcome, or any of a variety of reasons which do not justify authorization the process thereby ends 68. Alternatively, the approval may be withheld based upon what is believed to be an inappropriate assessment by the primary care physician. In that case, the assessment process is reinitiated 64 and the primary care physician bears the responsibility to reassess the patient's condition and determine, possible with greater precision or the use of more cost-effective utilization practices, whether the patient's condition warrants submitting a new code that reflects a more appropriate course of action. As per the embodiments discussed above, in the practice of the present invention it is preferred that a single, specific code be submitted to thus substantially reduce, if not eliminate, the susceptibility of the methods of the present invention to introduce abusive billing practices and the like.

To the extent such additional services and/or the use of one or more specialists is deemed warranted and hence approved, in the third possible outcome, an evaluation 76 is then made regarding the clinical options available within the network infrastructure that can most efficiently and cost-effectively render the medical services necessary to treat the specific condition of the patient. As part of such evaluation of the clinical options available, a variety of conventional practices may be used such that most cost-effective delivery system is utilized, such as which particular in-patient/out-patient services and/or specialists can be utilized to most efficiently and cost effectively render the applicable services. For example, practices such as capitation and usual and customary reductions can be utilized in regard to the treatment options that may ultimately be authorized.

Once a particular treatment has been authorized 78, which preferably will involve the use of a specifically designated service and/or specialist, the methods of the present invention provide for a continuous assessment of the administration of such treatment 84. In this regard, the patient undergoing treatment is closely monitored to insure that the treatment being administered is bringing about the desired clinical outcome, as well as is being administered in the most cost-effective manner given the resources available within the network infrastructure. Per the other steps in the method of the present invention requiring evaluation, it is contemplated that such assessment will be made by a competent staff of hospitalists and case managers that are continuously available to monitor and assess every aspect of the administration of the treatment authorized, as well as evaluating such administration from the standpoint of the costs associated with such administration and whether or not other cost alternatives may be available to provide the same quality of care to the patient at a lower cost. Advantageously, the methods of the present invention thus enable not only high quality care to be administered but that such high quality care is continuously administered in the most cost-effective manner possible such that utilization of resources within the network are continuously conserved.

As part of the assessment made with respect to the ongoing administration of treatment, continuous evaluation is made with respect to whether or not there are any ongoing clinical events necessary to provide adequate treatment or care for a particular patient's condition. In certain matters, such as the acute treatment of a particular condition requiring the use of specialists and either out-patient or in-patient services, such as surgical procedures and the like, generally no further care will be provided following the patient's recovery. In such circumstances, the delivery of health care, and hence utilization of resources, ends.

In order to treat chronic conditions, such as diabetes, cancer, Alzheimer's disease, or any other of a variety of conditions requiring continuous care, an ongoing obligation or decision making process 82 is continuously imposed with respect to the ongoing delivery of care necessary to treat such conditions that, pursuant to the methods discussed above, require strict adherence to the coding practices discussed herein. In this regard, to the extent a patient's condition warrants ongoing clinical events, such as the administration of particular types of intravenous medications, dialysis, and the like, each service that must necessarily be performed to provide such ongoing care must first be requested via the submission of a code 84, which as discussed above, will comprise a specific, and preferably single CPT code that is directed to a specific service to be rendered. Such code will be evaluated 86 and again closely scrutinized to determine whether of not the code is indicative of appropriate treatment and accurately represents the extent of services to be rendered while also being closely to ensure that the requested services corresponding to the submitted code are not subject to any type of abusive billing practices.

Based upon the evaluation 86, a decision 88 is made as to whether or not to approve the services corresponding to the submitted code. To the extent the evaluation of the code warrants that the particular treatment is inappropriate or unjustified due to clinical and/or financial reasons, the assessment of the options of treatment is reconsidered 76 and the process regarding the patient's condition and whether or not the patient does, in fact, require ongoing care is reevaluated. In this regard, such reassessment will take into account all considerations regarding the patient's condition, as well as whether or not the originally submitted code fails to reflect the best and most cost-effective option available for ongoing care of the patient's condition. Such process may continue indefinitely until such time as either the patient is no longer in need of continuous treatment or until the most optimal utilization of resources is identified and approved. With respect to such approval 88, such ongoing treatment is evaluated in terms of those options available within the network infrastructure. As per other aspects of the present invention, such options are continuously evaluated such that the most efficient utilization of resources are chosen. Once options have been sufficiently evaluated, treatment is authorized and the appropriate care administered to the patient.

In addition to providing exceptionally efficient and cost-effective care to patients within the patient population that further highly conserves utilization of medical resources available to such patients, the methods of the present invention can further be utilized to assess the efficiency of the delivery of health care through such conventional mechanisms as medical loss ratios and the like. Additionally, data may be generated through the methods of the present invention to identify which health care administrators, and in particular primary care physicians, that are most efficient in utilizing resources within the network, as well as those providers that are inefficient and fail to follow coding procedures, are continuously denied approval, or are otherwise ineffectual in delivering optimal health care. Similar data may be collected with respect to other medical services utilized with respect to the practice of the present invention, including the cost and efficiency associated with particular in-patient/outpatient services and specialty physicians.

Still further, the continuous evaluation of resource utilization, as compared to the number of patients within the patient population, their respective health risk levels and ongoing need for medical care, can be utilized to determine the costs associated with the administration of health care, which may be useful in determining appropriate premiums and the like. Such data can further be utilized to modify the types of medical services that should be excluded from those services to be provided to patients within the patient population (e.g., surgical procedures that are deemed to produce only a moderately favorable patient outcome relative to the costs associated with such procedure).

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed is:

1. A method for administering health care to patients within a patient population such that utilization of health care resources available to care for said patients within said patient population are conserved, the method comprising the steps:
   a) generating said patient population, said generation of said patient population comprising the steps:
      i) receiving a request from an individual to become a patient within said patient population;
      ii) obtaining information from said individual in step (i), wherein said information is obtained by an in-person interview and wherein said information comprises demographic information related to said individual comprising the individual's age, sex, medical history and geographic vicinity pertaining to said individual's residence as well as the number of emergency room visits, number of hospitalizations and readmissions, patient pharmacy records, and medication compliance, storing such information in electronic medical records embodied on a computer readable medium;

iii) evaluating said data submitted in step (ii) via a computer capable of interpreting said electronic medical records;

iv) enrolling said individual as a patient within said patient population; and v) repeating steps (i)-(iv) for a multiplicity of individuals;

b) receiving a request from a patient within said patient population generated in step a) for medical services;

c) assessing said request made in step b) and determining whether said request substantiates a specified clinical event, wherein said assessment is made by a primary care physician;

d) electronically submitting only a single CPT code corresponding to a single, specified medical service to be rendered in response to the clinical event specified in step (c) via a data communications network;

e) evaluating the single code submitted in step (d) for clinical and financial appropriateness, wherein said evaluation is performed by a hospitalist or case manager that is other than the primary care physician, and wherein evaluating the single code submitted in step (d) comprises (i) evaluating the effectiveness or clinical importance of the service required to be rendered in relation to the code, (ii) evaluating whether the submitted code is applicable to those health care services that are covered by the patient's health care, and (iii) evaluating whether the code is susceptible to duplicative and/or unbundled billing practice or otherwise provides any financial interest to the primary care physician;

f) electronically responding to said submission made in step (d) based upon said evaluation made in step (e), said response comprising either approval or disapproval to proceed with rendering the requested service corresponding to said code submitted in step (d) via a data communications network;

g) assessing said request made in step (b) and determining whether said request substantiates the utilization of either in-patient services, out-patient services, referral to a specialist, or combinations thereof, wherein said assessment is made by a primary care physician and the in-patient services, out-patient services and services from the specialist are to be performed by a physician other than the primary care physician;

h) electronically submitting only a single CPT code corresponding to a single, specified medical service to be rendered in response to the utilization requested in step (g) via a data communications network;

i) evaluating the single code submitted in step (h) for clinical and financial appropriateness, wherein said evaluation is performed by a hospitalist or case manager that is other than the primary care physician, and wherein evaluating the single code submitted in step (h) comprises (i) evaluating the effectiveness or clinical importance of the service required to be rendered in relation to the code, (ii) evaluating whether the submitted code is applicable to those health care services that are covered by the patient's health care, and (iii) evaluating whether the code is susceptible to duplicative and/or unbundled billing practice or otherwise provides any financial interest to the primary care physician;

j) electronically responding to said submission made in step (h) based upon said evaluation made in step (i), said response comprising either approval or disapproval to proceed with rendering the requested service corresponding to the code submitted in step (h) via a data communications network; and k) when the patient has a chronic condition, repeating steps (g)-(j) to continuously assess the utilization of the in-patient services, out-patient services, and services of the specialist to provide treatment of the chronic condition.

2. The method of claim 1 wherein in step (a), substep (iii), said evaluation comprises comparing said information submitted in step (a), substep (ii) with eligibility criteria, said eligibility criteria defining a standard by which said individuals are compared for acceptance as a patient within said patient population.

3. The method of claim 2 wherein step (a), substep (iii), further comprises assessing the current state of health of said individual and anticipated future health of said individual by retrospectively examining the individual's prior medical history and prospectively examining the anticipated future medical needs of said individual.

4. The method of claim 1 wherein step (a), substep (iv), further comprises assigning a risk level to said patient.

5. The method of claim 4 wherein in step (a), substep (iv), said risk level assigned said patient is indicative of the anticipated utilization of resources said patient is projected to utilize while a member of said patient population.

6. The method of claim 5 wherein following step (a), substep (v), such process further comprises step:

(vi) periodically updating and reviewing information indicative of the health of said patients within said patient population and reassigning risk levels associated with said patients within said patient population.

7. The method of claim 6 wherein said reassigning of risk levels is performed every six months.

8. The method of claim 5 wherein step (a), sub step (iv) further comprises the step of charging a premium to said individual for becoming a member of said patient population.

9. The method of claim 8 wherein said premium corresponds to said risk level assigned to said patient.

10. The method of claim 1 wherein step (f) further comprises the step of determining whether to provide a reimbursement to said primary care physician for said services sought to be rendered in relation to said code submitted in step (c).

11. The method of claim 1 wherein in step (f) said disapproval of said services sought to be rendered in relation to said code submitted in step (c) is followed by the further step:

(a) repeating step (b)-(d).

12. The method of claim 1 wherein in step (c) said primary care physician is a member of a network of physicians contracted to render medical services on behalf of a health plan, health maintenance organization, or government sponsored health care program.

13. The method of claim 1 wherein in step (c), said code corresponds to a single medical service to be rendered exclusively by said physician.

14. The method of claim 1 wherein in step (a), substep (ii), said number of emergency room visits and number of hospitalizations and readmissions are determined with respect to the twelve month period preceding obtaining the information.

15. The method of claim 1 wherein step (a), substep (ii) further comprises obtaining information in relation to the current condition of any disease that said individual may have.

16. The method of claim 15 wherein said disease is hypertension.

17. The method of claim 15 wherein said disease is diabetes.

18. The method of claim 1 wherein the request for medical services in step (b) is in relation to the treatment of a chronic condition requiring continuous care.

19. The method of claim 18 wherein the chronic condition is selected from the group consisting of diabetes, cancer, and Alzheimer's disease.

20. The method of claim 18 wherein each specified clinical event assessed in step (c) is submitted as a single code every single time the specified clinical event is required until the specified clinical event is no longer required.

21. A method for administering an integrated health care delivery system for providing comprehensive health care to a patients within a patient population such that utilization of health care resources available to care for said patients within said patient population are conserved, the method comprising the steps:
  a) generating said patient population, said generation of said patient population comprising the steps:
    i) receiving a request from an individual to become a patient within said patient population;
    ii) obtaining information from said individual in step (i), wherein said information is obtained by an in-person interview and wherein said information comprises demographic information related to said individual comprising the individual's age, sex, medical history and geographic vicinity pertaining to said individual's residence as well as the number of emergency room visits, number of hospitalizations and readmissions, patient pharmacy records, and medication compliance, storing such information in electronic medical records embodied on a computer readable medium;
    iii) evaluating said data submitted in step (ii) via a computer capable of interpreting said electronic medical records;
    iv) enrolling said individual as a patient within said patient population; and
    v) repeating steps (i)-(iv) for a multiplicity of individuals;
  b) receiving a request from a patient within said patient population for medical services;
  c) assessing said request made in step b) and determining whether said request substantiates the utilization of either in-patient services, out-patient services, referral to a specialist, or combinations thereof, wherein said assessment is made by a primary care physician;
  d) electronically submitting only a single CPT code corresponding to a single, specified medical service to be rendered in response to the utilization requested in step (c) via a data communications network;
  e) evaluating the single code submitted in step (d) for clinical and financial appropriateness, wherein said evaluation is performed by a hospitalist or case manager that is other than the primary care physician, and wherein evaluating the single code submitted in step (d) comprises (i) evaluating the effectiveness or clinical importance of the service required to be rendered in relation to the code, (ii) evaluating whether the submitted code is applicable to those health care services that are covered by the patient's health care, and (iii) evaluating whether the code is susceptible to duplicative and/or unbundled billing practice or otherwise provides any financial interest to the primary care physician;
  f) electronically responding to said submission made in step (d) based upon said evaluation made in step (e), said response comprising either approval or disapproval to proceed with rendering the requested service corresponding to said code submitted in step (c) via a data communications network; and
  g) when the patient has a chronic condition, repeating steps (c)-(f) to continuously assess the utilization of the in-patient services, out-patient services, and services of the specialist to provide treatment of the chronic condition.

22. The method of claim 21 wherein in step (f) said disapproval of said services sought to be rendered in relation to said code submitted in step (c) is followed by the further step:
  (a) repeating step (b)-(d).

23. The method of claim 21 wherein in step (a) said primary care physician is a member of a network of physicians contracted to render medical services on behalf of a health plan, health maintenance organization, or government sponsored health care program.

* * * * *